US006451285B2

(12) United States Patent
Blondino et al.

(10) Patent No.: US 6,451,285 B2
(45) Date of Patent: *Sep. 17, 2002

(54) SUSPENSION AEROSOL FORMULATIONS CONTAINING FORMOTEROL FUMARATE AND A FLUOROALKANE PROPELLANT

(75) Inventors: Frank E. Blondino, Plantation; Michael Brucato, Miami Shores; Maria W. Buenafe, Miami Beach, all of FL (US)

(73) Assignee: Baker Norton Pharmaceuticals, Inc., Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 7 days.

(21) Appl. No.: 09/099,779

(22) Filed: Jun. 19, 1998

(51) Int. Cl.[7] .................................................. A61K 9/12
(52) U.S. Cl. ............................ 424/45; 424/46; 424/489
(58) Field of Search ............................ 424/45, 46, 489

(56) References Cited

U.S. PATENT DOCUMENTS

| | | | | |
|---|---|---|---|---|
| 3,014,844 A | | 12/1961 | Thiel et al. | |
| 4,174,295 A | | 11/1979 | Bargigia et al. | |
| 5,190,029 A | | 3/1993 | Byron et al. | |
| 5,225,183 A | * | 7/1993 | Purewal et al. | 424/45 |
| 5,492,688 A | | 2/1996 | Byron et al. | 424/45 |
| 5,508,023 A | | 4/1996 | Byron et al. | 424/45 |
| 5,605,674 A | | 2/1997 | Purewal et al. | |
| 5,674,473 A | | 10/1997 | Purewal et al. | |
| 5,683,677 A | | 11/1997 | Purewal et al. | |
| 5,695,743 A | | 12/1997 | Purewal et al. | |
| 5,736,124 A | * | 4/1998 | Akehurst et al. | 424/45 |
| 5,776,432 A | | 7/1998 | Schultz et al. | |
| 5,914,122 A | * | 6/1999 | Otterbeck et al. | |
| 6,004,537 A | * | 12/1999 | Blondino et al. | |
| 6,039,932 A | * | 3/2000 | Govind et al. | |

FOREIGN PATENT DOCUMENTS

| | | |
|---|---|---|
| DE | 41 23 663 A1 | 1/1993 |
| EP | 0 504 112 A2 | 3/1992 |
| EP | 0 550 031 A1 | 7/1993 |
| EP | 0 553 298 B1 | 11/1994 |
| EP | 0536235 | 1/1997 |
| WO | 91/11173 | 9/1991 |
| WO | 92/22286 | 12/1992 |
| WO | 93/11747 | 6/1993 |
| WO | 93/11773 | 6/1993 |
| WO | 96/19198 | 6/1996 |
| WO | 97/47286 | 12/1997 |
| WO | WO 98/15280 | 4/1998 |
| WO | 98/24420 | 6/1998 |

OTHER PUBLICATIONS

Atkins et al. (1992) Design and Development of Inhalation Drug Delivery Systems, *Pharmaceutical Inhalation Aerosol Technology*, pp. 155–185.
Byron et al. (1990) Aerosol Formulation, Generation, and Delivery Using Metered Systems, *Respiratory Drug Delivery*, Chapter 7, pp. 167–205.
Byron et al. (1994) Some Aspects of Alternative Propellant Solvency, *Respiratory Drug Delivery IV*, pp. 231–242.
Dalby et al. (1988) *Pharmaceutical Research* 5:36–39.
Daly et al. (1993) *Spray Technology & Marketing* 3:34–38.
June et al. (1994) *Pharmaceutical Technology* 18:40–52.
Leach (1996) Enhanced Drug Delivery Through Reformulating MDIs with HFA Propellants–Drug Deposition and Its Effect on Preclinical and Clinical Programs, *Respiratory Drug Delivery V* , pp. 133–144.
Molina et al. (1974) *Nature 249*:810–812.
Moren (1985) *Aerosol Dosage Forms and Formulations, Aerosols in Medicine*, Principles Diagnosis and Therapy, pp. 261–287.
Soine et al. (1992) *Journal Biopharm. Sci. 3*(102):41–47.
Thiel (1996) From Susie's Question to CFC Free: An Inventor's Perspective on Forty Years of MDI Development and Regulation, *Respiratory Drug Delivery V*, pp. 115–123.
Whitman et al. (1994) Alternative Propellant's: Proprietary Rights, Toxicological Issues and Projected Licensing Problems, *Respiratory Drug Delivery IV*, pp. 203–209.
Montreal Protocol of Substances Deplete the Ozone Layer, *Message From the President of The United States*, Dec. 21, 1987, 100th Congress, 1st Session, Senate, Treaty Doc 100–10.
Zurer et al. (1993) *Chemical& Engineering News 71*:12–18.

* cited by examiner

*Primary Examiner*—Raj Bawa

(57) ABSTRACT

Provided are pressurized metered dose inhalers containing stable formulations of a β-agonist drug in suspension or solution. Also provided are aerosol formulations suitable for inhalation therapy containing a β-agonist drug in suspension or solution.

1 Claim, 2 Drawing Sheets

SUSPENSION AEROSOL FORMULATIONS CONTAINING FORMOTEROL FUMARATE AND A FLUOROALKANE PROPELLANT

FIELD OF THE INVENTION

The invention relates to pressurized metered dose inhalers and aerosol formulations for inhalation therapy.

BACKGROUND OF THE INVENTION

Because of environmental considerations, chlorohydrocarbon and chlorofluorocarbon propellants for aerosol formulations for medical uses have been largely replaced by hydrofluoroalkanes such as 1,1,1,2-tetrafluoroethane ("HFA-134a") and 1,1,1,2,3,3,3,-heptafluoropropane ("HFA-227ea") that have been identified as safe for use in pressurized metered dose inhalers.

Such medicinal aerosol formulations are generally of the solution or suspension type. Each type is composed of, at least, the medicament and the propellant. Some formulations also include one or more special purpose adjuvants such as a cosolvent or a surfactant (EP 0 372777). Conventional aerosol solution formulations contain low concentrations of a cosolvent more polar than the propellant. Conventional aerosol suspension formulations contain a surfactant rather than a cosolvent on a theory that the surfactant would prevent agglomeration of the particles, their adhesion to the walls of the aerosol container, and provide for lubrication of the dispensing valve ("actuator"). (U.S. Pat. No. 3,014,844).

Ethanol has been used as a cosolvent. However, previous teachings (see, e.g., EP 0 616525) have taught away from using concentrations of ethanol greater than 5% for solution aerosol formulations for β-agonists. Historically, ethanol concentrations greater than 5% have been used only for steroid-based formulations with hydrofluoroalkane propellants.

The β-agonist drug, formoterol ("eformoterol" in Europe) and its derivatives, have proven difficult to formulate in conventional aerosols. Such formulations have exhibited short shelf-lives and require refrigeration. Refrigeration is undesirable because many patients are required to carry the aerosol canisters on their persons. There remains, therefore, an important need for aerosol formulations for β-agonist drugs such as formoterol and its derivatives that remain chemically and physically stable during storage at ambient conditions of temperature and humidity.

SUMMARY OF THE INVENTION

An objective of the present invention is to provide a pressurized metered dose inhaler that contains a stable formulation of a β-agonist drug, which does not require the use of refrigeration.

Another objective of the present invention is to provide a stable formulation of a β-agonist drug that is suitable for use as an aerosol, which does not require the use of refrigeration.

The above objectives and other objectives are surprisingly achieved by the following. The present invention provides a novel pressurized metered dose inhaler comprising a container equipped with a metering valve and containing a pressurized aerosol formulation formulated from a composition comprising:
 a β-agonist drug;
 at least one fluoroalkane propellant; and
 greater than 5% by weight, based on total weight of the aerosol formulation, of a solvent that is capable of solubilizing or dissolving the β-agonist drug.

The invention further provides a novel pressurized metered dose inhaler comprising a container equipped with a metering valve and containing a pressurized aerosol formulation formulated from a composition comprising:
 particles of a β-agonist drug;
 at least one fluoroalkane propellant; and
 a surfactant that is capable of forming a suspension of the particles of β-agonist drug.

The invention also provides a novel aerosol formulation adapted for use in a pressurized aerosol container, said aerosol formulation being formulated from a composition comprising:
 a β-agonist drug;
 at least one fluoroalkane propellant; and
 greater than 5% by weight, based on total weight of the aerosol formulation, of a solvent that is capable of solubilizing or dissolving the β-agonist drug.

The invention further provides a novel aerosol formulation adapted for use in a pressurized aerosol container, said aerosol formulation being formulated from a composition comprising:
 particles of a β-agonist drug;
 at least one fluoroalkane propellant; and
 a surfactant that is capable of forming a suspension of the particles of β-agonist drug.

The aerosol formulations are surprisingly stable under conditions up to about 40° C. and about 75% relative humidity for at least about four weeks.

DETAILED DESCRIPTION OF THE INVENTION

Figure 1:
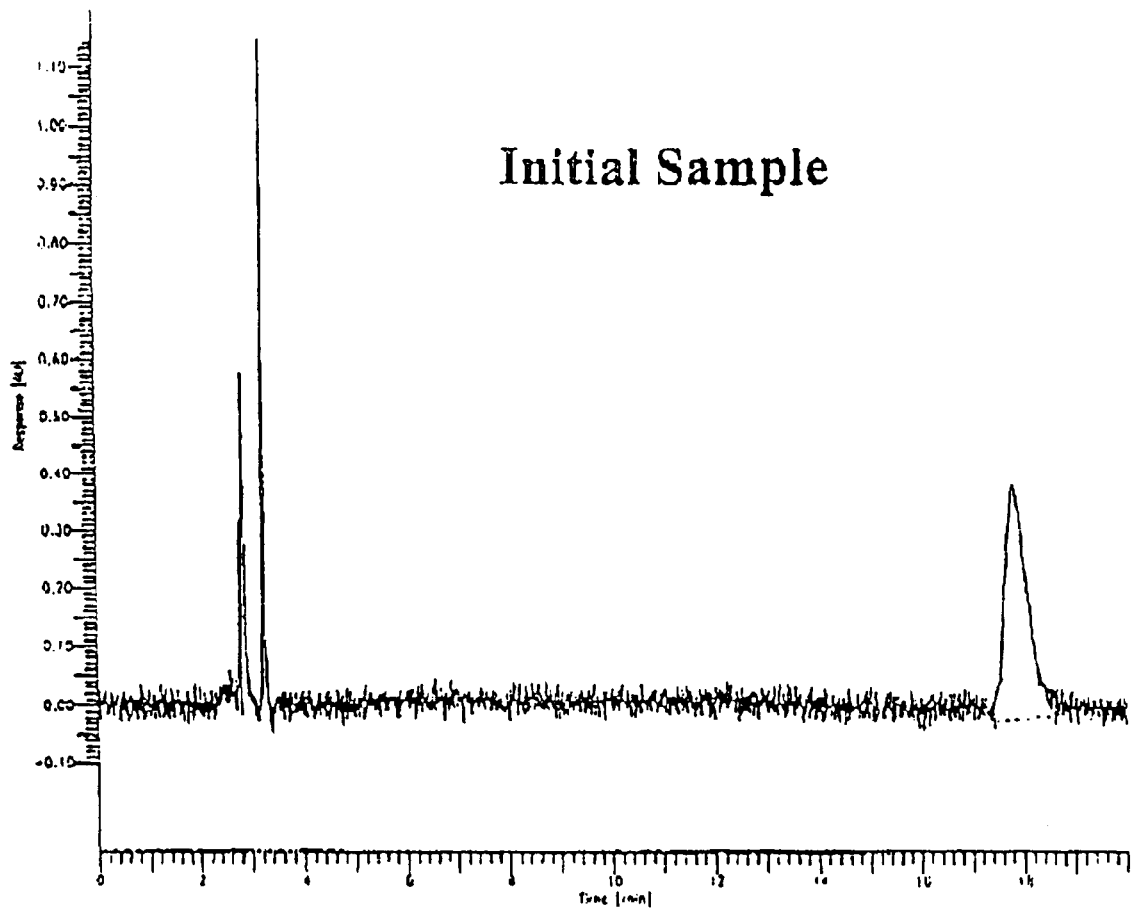
FIG. 1 illustrates a chromatogram of formoterol fumarate formulated as a suspension.

It has been unexpectedly discovered that the stability of aerosol formulations of solutions of a β-agonist drug can be significantly improved by utilizing more than 5% by weight of a solvent capable of solubilizing or dissolving the β-agonist drug. The β-agonist drug can be any form that is suitable for application to the lungs or nasal passages of a human, such as base form or weak acid form. The present invention will be described with reference to the β-agonist drug formoterol. The term "formoterol" is hereinafter understood to mean the base form of formoterol as well as the weak acid form of formoterol, unless stated otherwise. A preferred weak acid form of formoterol is formoterol fumarate.

The amount of β-agonist drug utilized in the aerosol formulation will depend on the type of drug selected. For formoterol fumarate, the concentration utilized is usually about 1% by weight or less, preferably about 0.01% to about 0.02% by weight, based on the total weight of the aerosol formulation.

Any solvent that is suitable for inhalation and capable of solubilizing or dissolving the selected β-agonist drug can be used. Examples of suitable solvents include alcohols, ethers, hydrocarbons, and perfluorocarbons. Preferably the solvent is short chain polar alcohols. More preferably, the solvent is an aliphatic alcohol having from one to six carbon atoms, such as ethanol and isopropanol. The most preferred solvent is ethanol. Examples of suitable hydrocarbons include n-butane, isobutane, pentane, neopentane and isopentanes. Examples of suitable ethers include dimethyl ether and diethyl ether. Examples of suitable perfluorocarbons include perfluoropropane, perfluorobutane, perfluorocyclobutane, and perfluoropentane.

The solvent is usually present in an amount of from about 6% to about 30% by weight, based on the total weight of the aerosol formulation. Preferably, the solvent is present in an amount of about 10% to about 15% by weight. Based on the disclosure provided herein, one skilled in the art will recognize that lower concentrations of medicament usually require lower concentrations of solvent, and vice versa, in order to form a stable solution.

Any fluoroalkane propellant that is suitable for inhalation can be used. Examples of suitable fluoroalkanes include HFA-134a, HFA-227ea, HFA-125 (pentafluoroethane), HFA-152a (1,1-difluoroethane), and HFA-32 (difluoromethane). Hydrocarbon and/or aliphatic gases may be added to modify propellant characteristics as required. Preferably, the aerosol formulation is substantially free of chlorofluorocarbons. However, if desired chlorofluorocarbons can be utilized.

The propellant for solution formulations is usually present in an amount of from about 70% to about 94% by weight, based on the total weight of the aerosol formulation. A preferred aerosol formulation comprises HFA-134a in an amount less than about 90% by weight, ethanol in an amount greater than about 10% by weight, and formoterol fumarate in an amount of about 0.01% by weight. A particularly preferred aerosol formulation comprises about 85% by weight of HFA-134a, about 15% by weight of ethanol, and about 0.01% by weight of formoterol fumarate.

Pressurized metered dose inhalers are now well known in the art. Any pressurized metered dose inhaler that is suitable for application of drugs to the lungs or nose of a patient can be used. Pressurized metered dose inhalers usually are equipped with a metering valve having a spray orifice diameter of about 460 µm. However, with the higher concentrations of solvent employed in the present invention, it may be desirable that the solvent evaporates as soon as possible after inhalation. This can be achieved by reducing the spray orifice diameter, for example, to 250 µm, in combination with using solvent concentrations of about 10 to about 15% by weight. Based on the disclosure provided herein, one skilled in the art will be able to adjust the component composition to deliver a desired dose for the selected metered valve, without undue experimentation. For example, the composition may be altered to adjust the vapor pressure of the formulation. The aerosol formulation and metering valve are usually selected to provide a therapeutically effective amount of the β-agonist drug per activation. An example of a therapeutically effective amount of formoterol fumarate is about 12 µg per activation.

It has also been unexpectedly discovered that stable aerosol formulations of suspensions of particles of a β-agonist drug can be formed by utilizing the β-agonist drug in combination with a surfactant that is capable of forming a suspension of the β-agonist drug particles. The present invention will be described with reference to the β-agonist drug formoterol.

The propellant can be any of the propellants described herein with reference to solution aerosol formulations. However, the propellant in suspension aerosol formulations can be utilized in amounts up to about 99.9% by weight, based on the total weight of the aerosol formulation.

The amount of β-agonist drug utilized in the aerosol formulation will depend on the type of drug selected. For formoterol fumarate, the concentration utilized is usually about 1% by weight or less, preferably about 0.01% to about 0.02% by weight, based on the total weight of the aerosol formulation.

The particle size of the β-agonist drug should be suitable for inhalation into the nose or lung. Suitable average particle sizes are about 100 µm and less, preferably about 20 µm and less, and more preferably in the range of about 1 to about 10 µm.

Any surfactant that is suitable for application to the lungs of a patient and which is capable of forming a suspension of particles of the β-agonist drug can be utilized. Examples of suitable surfactants include polyalcohols such as polyethylene glycol (PEG 300), diethylene glycol monoethyl ether (Transcutol), polyoxyethylene(20) sorbitan monolaurate (Tween 20) or monooleate (Tween 80), propoxylated polyethylene glycol (Antarox 31R1), polyoxyethylene 4-lauryl ether (Brij 30), and surfactants having similar HLBs. Preferably, the surfactant is polyoxyethylene 4-lauryl ether (Brij 30). The surfactant is usually present in an amount of about 1% by weight or less.

A preferred suspension formulation comprises HFA-134a in an amount greater than 99% by weight, Brij 30 surfactant in an amount of about 0.002% by weight or greater, and formoterol fumarate in an amount of about 1% or less. A particularly preferred suspension formulation comprises about 99% by weight of HFA-134a, about 0.02% by weight of Brij 30, and about 0.02% by weight of formoterol fumarate. A particularly preferred formulation in a 19 ml canister comprises about 12.6 g/canister of HFA-134a, about 0.002 g/canister Brij 30, and about 0.002 g/canister of formoterol fumarate.

The following examples are presented merely to illustrate particular embodiments of the invention and not to limit the claims which are supported by the entire specification.

EXAMPLES 1–3

Three suspension aerosols according the present invention were formulated by combining the components shown in Table 1, using the following steps:

1. Weighing the solvent or surfactant into a plastic coated glass bottle or an aluminum canister.
2. Adding the weighed drug.
3. Crimping a valve upon the bottle or canister.
4. Adding a known amount of propellant through the valve into the bottle or canister.
5. Sonicating the formulation for about 5 minutes.

A Presspart, 19 mL, aluminum metered dose inhaler canister with a Bespak BK357, 63 µL metered valve was used, unless otherwise stated.

The properties of the Example aerosol formulations were tested using one or more of the following:

appearance (no external signs of leaking or deformation should be present);

leakage to meet United States Pharmacopeia 23 and National Formulary 18 standards;

canister contents to be within 10% of the mean;

drug per container to be within 25% of the mean;

chemical assay to be within 90.0–110% of label claim;

weight per metered dose;

unit spray content and content uniformity to meet Pharmacopeial Forum, vol. 22, no. 6 standards; and aerodynamic size distribution and water determination.

The test results are shown in Table 1. By comparing the percent deposition in Stage 2, it was determined that formulations containing Brij 30 and Tween 20 were superior to those containing PEG 300. In addition, the data demonstrated that the Tween 20 formulation deposited a greater amount of drug on the actuator. Therefore, in order to minimize deposition on this type of actuator, Brij 30 was a more useful surfactant in these formulations than was Tween 20.

EXAMPLES 4–7

Four solution aerosols according to present invention were formulated by combining the components shown in Table 2, using the method described in Example 1. To determine the stability of the solution aerosol formulations, Examples 6 and 7 were maintained for 1 month (28 days) at 40° C. and 75% relative humidity, which are considered herein as accelerated conditions. The solution aerosol formulations were equilibrated at room temperature overnight before testing. The properties of the solution aerosol formulations were measured as in Example 1 and the results are shown in Table 2.

The data indicates that the dose delivered (by unit spray determination) after storage under accelerated conditions was lower than that obtained with the initial samples due to drug adsorption onto the valve gasket material. However, the solution aerosol formulations showed no signs of chemical deterioration.

EXAMPLES 8 and 9

Two solution aerosols according to present invention were formulated by combining the components shown in Table 3, using the method described in Example 1. To determine the stability of the solution aerosol formulations, Example 9 was maintained for 1 month (28 days) at 40° C. and 75% relative humidity, which are considered herein as accelerated conditions. The solution aerosol formulations were equilibrated at room temperature overnight before testing. The properties of the solution aerosol formulations were measured as in Example 1 and the results are shown in Table 3.

The drug could not be recovered from the gasket materials during this study, which resulted in a loss of about 15% by weight. However, the solution aerosol formulations showed no signs of chemical deterioration.

EXAMPLES 10–13

Four suspension aerosols according to present invention were formulated by combining the components shown in Table 4, using the method described in Example 1. To determine the stability of the suspension aerosol formulations, Examples 12 and 13 were maintained for 1 month (28 days) at 40° C. and 75% relative humidity, which are considered herein as accelerated conditions. The suspension aerosol formulations were equilibrated at room temperature overnight before testing. The properties of the suspension aerosol formulations were measured as in Example 1 and the results are shown in Table 4.

After 28 days storage, the dose delivered (by unit spray determination) in Examples 12 and 13 was less than that obtained with the initial Examples 10 and 11, but not reduced by the same degree as with the solution formulation examples.

EXAMPLES 14–17

Four suspension aerosols according to present invention were formulated by combining the components shown in Table 5, using the method described in Example 1. To determine the stability of the suspension aerosol formulations, Examples 16 and 17 were maintained for 1 month (28 days) at 40° C. and 75% relative humidity, which are considered herein as accelerated conditions. The suspension aerosol formulations were equilibrated at room temperature overnight before testing. The properties of the suspension aerosol formulations were measured as in Example 1 and the results are shown in Table 5.

The test data demonstrates that there was about a 10% loss of drug after storage under accelerated conditions in Examples 16 and 17, relative to the initial Examples 14 and 15. This value is within acceptable limits and was in the area of 100% material balance (canister contents—drug per canister). In addition, the USP accepted method for determining particle size (Andersen impacter) was employed. The results showed that there was no chemical (as appearance of a known degradation product or loss of parent compound) or physical instability after storage including (1) as an increase in particle size (MMAD-mass median aerodynamic diameter), (2) change in the distribution (GSD-geometric standard deviation), (3) change in fine particle dose, or (4) change in fine particle fraction.

EXAMPLES 18 and 19

Two suspension aerosols according to present invention were formulated by combining the components shown in Table 6, using the method described in Example 1. The properties of the suspension aerosol formulations were measured as in Example 1 and the results are shown in Table 6.

EXAMPLE 20

Figure 2:
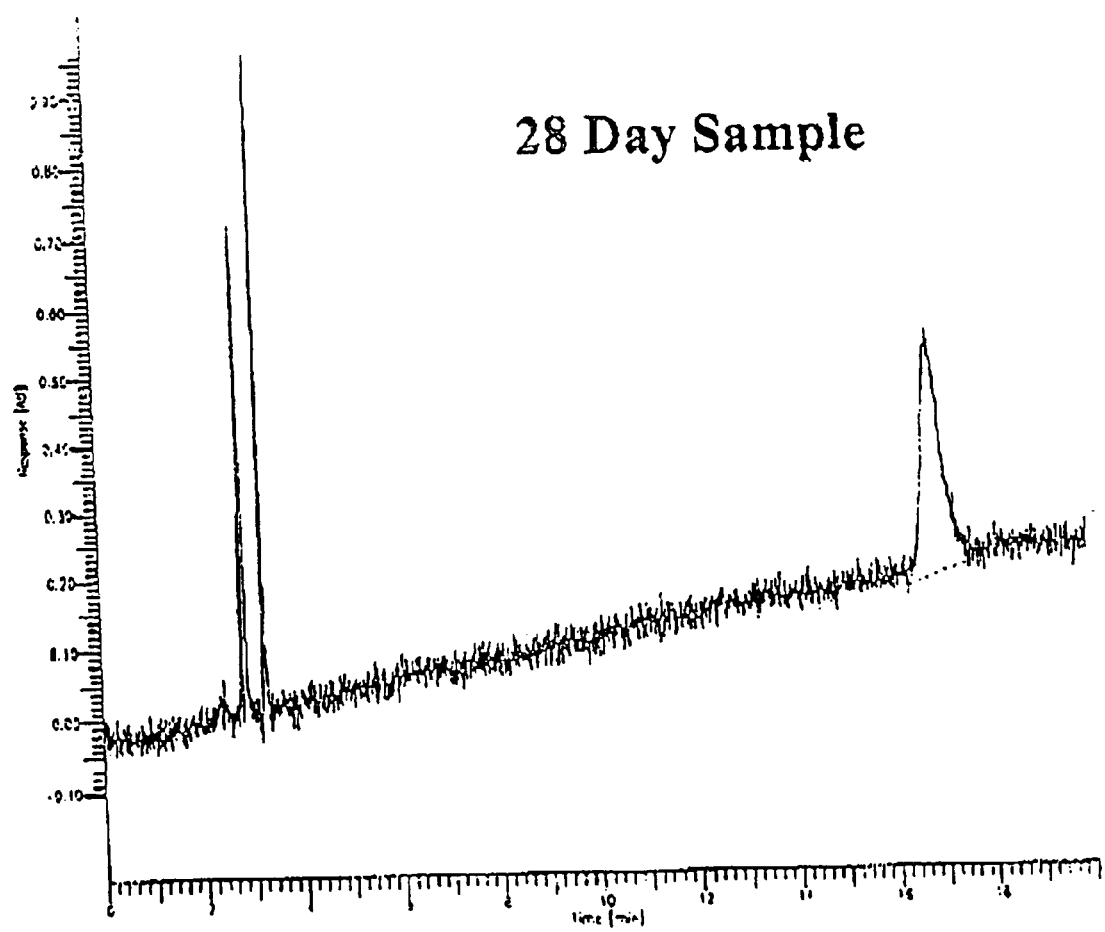
FIG. 2 illustrates a chromatogram of the formoterol fumarate after storage for 28 days at 40° C. and 75% relative humidity.

A suspension aerosol formulation was formed by combining 99.96% by weight of HFA-134a, 0.02% by weight formoterol fumarate, and 0.02% by weight of Brij 30, using the method described in Example 1. HPLC chromatograms of the suspension aerosol, before and after storage for 28 days at 40° C. and 75% relative humidity, were obtained as FIGS. 1 and 2 respectively. In each Figure, only a single peak, representing the intact drug, was observed. No peaks representing breakdown products of the drug (expected to be at about 13 minutes) were found. Thus, the formoterol suspension aerosol exhibited long term stability.

TABLE 1

| Test | | Example 1 | Example 2 | Example 3 |
|---|---|---|---|---|
| Unit Spray | Drug per Dose (mcg) | 8.27 | 8.53 | 5.97 |
| Content | Shot Weight (mg) | 82.15 | 81.10 | 80.70 |
| Single Stage | Valve/Actuator (mcg) | 26.59 | 40.73 | 11.27 |
| Liquid | Throat/Neck (mcg) | 25.00 | 16.36 | 13.59 |
| Impinger | Stage 1 (mcg) | 7.94 | 7.99 | 4.96 |
| | Stage 2 (mcg) | 40.87 | 39.92 | 27.71 |
| | Material Balance (%) | 66.50 | 73.50 | 41.60 |
| | % in Stage 2 | 40.71 | 38.02 | 48.17 |
| | Shot Weight (mg) | 80.80 | 78.90 | 77.90 |
| Formulation | HFA-134a | 8.55550 | 8.71860 | 8.53550 |
| | Surfactant | 0.0017 | 0.0017 | 0.0018 |
| | | (B3) | (T2) | (P3) |
| | Formoterol fumarate | 0.00080 | 0.00079 | 0.00076 |

B3-Brij ® 30
T2-Tween ® 20
P3-Polyethylene glycol 300

TABLE 2

| Test | | Initial Data | | 28 Day Data | |
|---|---|---|---|---|---|
| | | Example 4 | Example 5 | Example 6 | Example 7 |
| Unit Spray Content | Drug per Dose (mcg) | 5.21 | 4.81 | 4.37 | 4.26 |
| | Material Balance (%) | 90 | 84 | 78 | 72 |
| | Shot Weight (mg) | 72.05 | 70.35 | 72.58 | 71.38 |
| | Shot Number | 7–10 | 7–10 | 6–9 | 11–14 |
| Shot Weight | Shot Weight (mg) | 70.0 | 71.3 | 74.9 | 73.1 |
| | Shot Number | 21–25 | 10–14 | 20–24 | 35–39 |
| Single Stage Liquid Impinger | Valve/Actuator (mcg) | 6.14 | 0.00 | 0.00 | 0.00 |
| | Throat/Neck (mcg) | 38.63 | 36.67 | 27.96 | 46.47 |
| | Stage 1 (mcg) | 4.00 | 3.69 | 2.44 | 0.00 |
| | Stage 2 (mcg) | 56.54 | 54.99 | 38.81 | 37.37 |
| | Material Balance (%) | 91 | 80 | 58 | 70 |
| | % in Stage 2 | 53.69 | 57.67 | 56.08 | 44.57 |
| | Shot Weight (mg) | 72.10 | 72.96 | 76.39 | 72.60 |
| | Shot Number | 68–87 | 64–83 | 60–79 | 15–34 |
| Unit Spray Content | Drug per Dose (mcg) | 5.90 | 5.53 | 4.58 | 4.33 |
| | Material Balance (%) | 102 | 93 | 77 | 72 |
| | Shot Weight (mg) | 72.05 | 72.48 | 76.52 | 73.10 |
| | Shot Number | 54–57 | 54–57 | 51–54 | 51–57 |
| Shot Weight | Shot Weight (mg) | 71.1 | 72.3 | 77.0 | 73.8 |
| | Shot Number | 58–62 | 54–58 | 55–59 | 55–59 |
| Moisture Content | Moisture (ppm) | 442.08 | 624.41 | — | — |
| Unit Spray Content | Drug per Dose (mcg) | 6.24 | 6.13 | 5.42 | 4.79 |
| | Material Balance (%) | 107 | 104 | 92 | 79 |
| | Shot Weight (mg) | 72.28 | 72.42 | 75.80 | 73.52 |
| | Shot Number | 113–116 | 109–112 | 101–102 | 101–104 |
| Shot Weight | Shot Weight (mg) | 71.5 | 72.9 | 76.0 | 72.4 |
| | Shot Number | 122–126 | 118–122 | 108–112 | 110–114 |
| Formulation | HFA-134a | 16.912 | 17.064 | 17.224 | 16.753 |
| | Ethanol | 3.0062 | 3.0581 | 2.9963 | 3.0267 |
| | Formoterol fumarate | 0.00160 | 0.00164 | 0.00157 | 0.00163 |

TABLE 3

| Test | | Initial Data Example 8 | 28 Day Data Example 9 |
|---|---|---|---|
| Canister Contents | Drug per Canister (mg) | 1.597 | 1.324 |
| | % Recovery | 100 | 85 |
| Formulation | HFA-134a | 16.993 | 16.853 |
| | Ethanol | 3.0336 | 3.0269 |
| | Formoterol fumarate | 0.00159 | 0.00156 |

TABLE 4

| Test | | Initial Data | | 28 Day Data | |
|---|---|---|---|---|---|
| | | Example 10 | Example 11 | Example 12 | Example 13 |
| Unit Spray Content | Drug per Dose (mcg) | 14.45 | 14.22 | 13.32 | 11.10 |
| | Material Balance (%) | 92 | 89 | 85 | 77 |
| | Shot Weight (mg) | 80.0 | 82.9 | 80.75 | 80.75 |
| | Shot Number | 6–7 | 6–7 | 6–7 | 6–7 |
| Shot Weight | Shot Weight (mg) | 76.5 | 79.4 | 80.9 | 81.9 |
| | Shot Number | 8–12 | 8–12 | 18–22 | 8–12 |
| Single Stage Liquid Impinger | Valve/Actuator (mcg) | 32.72 | 31.36 | 23.36 | 27.90 |
| | Throat/Neck (mcg) | 31.21 | 27.93 | 19.11 | 17.47 |
| | Stage 1 (mcg) | 6.20 | 5.40 | 3.95 | 5.60 |
| | Stage 2 (mcg) | 75.95 | 76.92 | 78.58 | 69.57 |
| | Material Balance (%) | 94 | 90 | 78 | 83 |
| | % in Stage 2 | 51.99 | 54.32 | 62.86 | 57.72 |
| | Shot Weight (mg) | 79.1 | 81.7 | 82.1 | ND |
| | Shot Number | 13–22 | 13–22 | 8–17 | 18–27 |
| Unit Spray Content | Drug per Dose (mcg) | 15.03 | 15.49 | 13.72 | 13.42 |
| | Material Balance (%) | 96 | 99 | 87 | 92 |
| | Shot Weight (mg) | 79.7 | 81.4 | 81.4 | 81.2 |
| | Shot Number | 50–51 | 50–51 | 50–51 | 43–44 |
| Shot Weight | Shot Weight (mg) | 78.9 | 81.8 | 80.9 | 79.7 |
| | Shot Number | 52–56 | 52–56 | 52–56 | 52–56 |

TABLE 4-continued

|  |  | Initial Data | | 28 Day Data | |
| --- | --- | --- | --- | --- | --- |
| Test |  | Example 10 | Example 11 | Example 12 | Example 13 |
| Moisture Content | Moisture (ppm) | 428.91 | 342.21 | — | — |
| Unit Spray Content | Drug per Dose (mcg) | 13.58 | 12.67 | 10.55 | 14.73 |
|  | Material Balance (%) | 87 | 81 | 72 | 116 |
|  | Shot Weight (mg) | 79.4 | ND | 75.55 | 70.6 |
|  | Shot Number | 86–87 | 82–83 | 91–92 | 91–92 |
| Shot Weight | Shot Weight (mg) | 69.3 | 80.5 | 79.7 | 73.0 |
|  | Shot Number | 93–97 | 89–93 | 93–97 | 93–97 |
| Formulation | HFA-134a | 9.885 | 10.121 | 10.022 | 10.825 |
|  | Brij 30 | 0.00250 | 0.00227 | 0.00165 | 0.00152 |
|  | Formoterol fumurate | 0.00194 | 0.00195 | 0.00195 | 0.00194 |

TABLE 5

|  |  | Initial Data | | 28 Day Data | |
| --- | --- | --- | --- | --- | --- |
| Test |  | Example 14 | Example 15 | Example 16 | Example 17 |
| Canister Contents | Drug per Canister (mg) | 2.239 | — | 2.068 | — |
|  | % Recovery | 118 | — | 108 | — |
| Andersen Impactor | Valve (mcg) | — | 9.86 | — | 15.25 |
|  | Actuator/Adapter (mcg) | — | 19.35 | — | 9.37 |
|  | Induction Port/Cone (mcg) | — | 20.37 | — | 17.15 |
|  | Stage 0 (mcg) | — | 4.87 | — | 2.60 |
|  | Stage 1 (mcg) | — | 3.31 | — | 2.15 |
|  | Stage 2 (mcg) | — | 3.42 | — | 2.94 |
|  | Stage 3 (mcg) | — | 11.64 | — | 13.67 |
|  | Stage 4 (mcg) | — | 31.37 | — | 27.20 |
|  | Stage 5 (mcg) | — | 20.43 | — | 19.80 |
|  | Stage 6 (mcg) | — | 4.88 | — | 3.82 |
|  | Stage 7 (mcg) | — | 1.25 | — | 0.75 |
|  | Stage F (mcg) | — | 0.51 | — | 0.00 |
|  | Total S0–S7 (mcg) | — | 81.17 | — | 72.93 |
|  | Total Drug Recovered (mcg) | — | 131.26 | — | 114.70 |
|  | Material Balance (%) | — | 90 | — | 75 |
|  | MMAD | — | 2.5 | — | 2.5 |
|  | GSD | — | 1.9 | — | 1.7 |
|  | Fine Particle Dose (mcg) | — | 73.50 | — | 68.18 |
|  | Fine Particle Fraction (%) | — | 73 | — | 75 |
| Formulation | HFA-134a | 9.899 | 10.642 | 10.134 | 10.219 |
|  | Brij 30 | 0.00163 | 0.00221 | 0.00188 | 0.00241 |
|  | Formoterol fumarate | 0.00189 | 0.00189 | 0.00192 | 0.00192 |

TABLE 6

| Test |  | Example 18 | Example 19 |
| --- | --- | --- | --- |
| Unit Spray Content | Drug per Dose (mcg) | 10.87 | 9.55 |
|  | Material Balance (%) | 89.0 | 78.5 |
|  | Shot Weight (mg) | 78.6 | 78.0 |
|  | Shot Number | 6–7 | 71–72 |
| Unit Spray Content | Drug per Dose (mcg) | 10.51 | 12.90 |
|  | Material Balance (%) | 86.0 | 104.8 |
|  | Shot Weight (mg) | 78.7 | 78.9 |
|  | Shot Number | 8–9 | 73–74 |
| Andersen Impactor | Valve (mcg) | 5.93 | 9.14 |
|  | Actuator/Adapter (mcg) | 28.91 | 29.02 |
|  | Induction Port/Cone (mcg) | 30.03 | 20.18 |
|  | Stage 0 (mcg) | 1.33 | 0.96 |
|  | Stage 1 (mcg) | 1.64 | 1.32 |
|  | Stage 2 (mcg) | 2.28 | 1.72 |
|  | Stage 3 (mcg) | 9.54 | 8.45 |
|  | Stage 4 (mcg) | 29.37 | 27.25 |
|  | Stage 5 (mcg) | 27.71 | 27.52 |
|  | Stage 6 (mcg) | 3.27 | 3.38 |
|  | Stage 7 (mcg) | 0.00 | 0.00 |
|  | Stage F (mcg) | 0.68 | 0.00 |
|  | Total S0–S7 (mcg) | 75.14 | 70.60 |
|  | Total Drug Recovered (mcg) | 140.69 | 128.93 |
|  | Material Balance (%) | 107.7 | 103.8 |
|  | MMAD | 2.3 | 2.5 |
|  | GSD | 1.6 | 1.5 |
|  | Fine Particle Dose (mcg) | 73 | 68 |
|  | Fine Particle Fraction (%) | 69 | 75 |

TABLE 6-continued

| Test | | Example 18 | Example 19 |
|---|---|---|---|
| Andersen Impactor | Valve (mcg) | 5.64 | — |
| | Actuator/Adapter (mcg) | 28.58 | — |
| | Induction Port/Cone (mcg) | 23.56 | — |
| | Stage 0 (mcg) | 1.13 | — |
| | Stage 1 (mcg) | 1.56 | — |
| | Stage 2 (mcg) | 1.97 | — |
| | Stage 3 (mcg) | 9.95 | — |
| | Stage 4 (mcg) | 30.04 | — |
| | Stage 5 (mcg) | 27.51 | — |
| | Stage 6 (mcg) | 3.05 | — |
| | Stage 7 (mcg) | 0.00 | — |
| | Stage F (mcg) | 0.00 | — |
| | Total S0–S7 (mcg) | 75.21 | — |
| | Total Drug Recovered (mcg) | 132.98 | — |
| | Material Balance (%) | 103.3 | — |
| | MMAD | 2.5 | — |
| | GSD | 1.5 | — |
| | Fine Particle Dose (mcg) | 73 | — |
| | Fine Particle Fraction (%) | 74 | — |
| Formulation | HFA-134a | 12.8169 | 12.6705 |
| | Brij 30 | 0.00230 | 0.00220 |
| | Formoterol fumarate | 0.002044 | 0.001970 |

While the invention has been described in detail and with reference to specific embodiments thereof, it will be apparent to those of ordinary skill in the art that various changes and modifications can be made to the claimed invention without departing from the spirit and scope thereof.

What is claimed is:

1. A suspension aerosol formulation for delivery via a MDI, wherein said aerosol comprising:
   a. up to 1% by weight of particles of formoterol fumarate having an average particle size of from about 1 $\mu$m to about 10 $\mu$m;
   b. up to 99.9% of at least one fluoroalkane propellant selected from the group consisting of HFA-134a, HFA-227ea, HFA-125; HFA-152a and HFA-32; and
   c. up to 1% by weight or less of a surfactant selected from the group consisting of diethylene glycol monoethyl ether and polyoxyethylene 4-lauryl ether, wherein all weights are based on the total weight of the suspension aerosol formulation.

* * * * *